(12) United States Patent  
Potyrailo et al.

(10) Patent No.: US 7,977,660 B2
(45) Date of Patent: Jul. 12, 2011

(54) ARTICLE, DEVICE, AND METHOD

(75) Inventors: Radislav Alexandrovich Potyrailo, Niskayuna, NY (US); Scott Martell Boyette, New Hope, PA (US); Glenn Alfred Johnson, Devon, PA (US); William Guy Morris, Rexford, NY (US); Ronald James Wroczynski, Schenectady, NY (US); Andrew Michael Leach, Clifton Park, NY (US); Peter Miller, New London, CT (US); Caibin Xiao, Harleysville, PA (US)

(73) Assignee: General Electric Company, Niskayuna, NY (US)

( * ) Notice: Subject to any disclaimer, the term of this patent is extended or adjusted under 35 U.S.C. 154(b) by 599 days.

(21) Appl. No.: 12/045,217

(22) Filed: Mar. 10, 2008

(65) Prior Publication Data
US 2009/0044603 A1 Feb. 19, 2009

Related U.S. Application Data

(60) Provisional application No. 60/955,823, filed on Aug. 14, 2007.

(51) Int. Cl.
*G01N 33/00* (2006.01)
*G01N 15/00* (2006.01)
(52) U.S. Cl. ........ 250/573; 250/575; 250/576; 73/53.01
(58) Field of Classification Search .......... 250/573–577; 73/53.01, 61.48; 702/188, 30; 435/6; 436/169, 436/172; 356/436, 443
See application file for complete search history.

(56) References Cited

U.S. PATENT DOCUMENTS

| | | | |
|---|---|---|---|
| 6,245,508 B1 * | 6/2001 | Heller et al. | 435/6 |
| 6,296,020 B1 | 10/2001 | McNeely et al. | |
| 6,351,986 B1 | 3/2002 | Schwab | |
| 6,376,255 B1 | 4/2002 | Schwab et al. | |
| 6,379,621 B1 | 4/2002 | Schwab | |
| 6,515,594 B1 | 2/2003 | Rettig | |
| 6,655,223 B2 | 12/2003 | March et al. | |
| 6,678,045 B2 | 1/2004 | Rettig et al. | |
| 6,824,660 B2 | 11/2004 | Tomita | |
| 6,852,284 B1 | 2/2005 | Holl et al. | |
| 6,878,940 B2 | 4/2005 | Nakamura et al. | |
| 7,015,963 B2 | 3/2006 | Ebi | |
| 7,071,470 B2 | 7/2006 | Nomura et al. | |
| 7,100,427 B2 | 9/2006 | Kahn et al. | |

(Continued)

FOREIGN PATENT DOCUMENTS

EP 1506813 A1 2/2005

(Continued)

OTHER PUBLICATIONS

Potyrailo et al., "Analog Signal Acquisition From Computer Optical Disk Drives for Quantitative Chemical Sensing", Anal. Chem., vol. 78, No. 16, pp. 5893-5899, Aug. 15, 2006.

(Continued)

*Primary Examiner* — Kevin Pyo
(74) *Attorney, Agent, or Firm* — Paul J. DiConza

(57) ABSTRACT

An article includes a substrate assembly for use in a detector system. The substrate assembly includes a substrate; a sample reception structure secured to the substrate; a test window extending through the substrate; and a fluid channel defined by a surface of the substrate and extending from the sample reception structure to the test window.

23 Claims, 2 Drawing Sheets

U.S. PATENT DOCUMENTS

| | | |
|---|---|---|
| 7,101,661 B1 | 9/2006 | Heller et al. |
| 7,104,115 B2 | 9/2006 | Kahn et al. |
| 7,189,314 B1 | 3/2007 | Pace et al. |
| 7,249,000 B2 | 7/2007 | Kahn et al. |
| 7,297,962 B2 | 11/2007 | Baker et al. |
| 2003/0021725 A1 | 1/2003 | Unno et al. |
| 2003/0194215 A1 | 10/2003 | Tanaka et al. |
| 2003/0211012 A1 | 11/2003 | Bergstrom et al. |
| 2003/0218130 A1 | 11/2003 | Boschetti et al. |
| 2004/0141884 A1 | 7/2004 | Unno et al. |
| 2004/0157149 A1 | 8/2004 | Hofmann |
| 2005/0111000 A1 | 5/2005 | Potyrailo et al. |
| 2005/0247113 A1 | 11/2005 | Kahn et al. |
| 2005/0251366 A1 | 11/2005 | Kahn et al. |
| 2006/0020427 A1 | 1/2006 | Kahn et al. |
| 2006/0194215 A1 | 8/2006 | Kronick et al. |
| 2007/0050157 A1 | 3/2007 | Kahn et al. |
| 2007/0080976 A1 | 4/2007 | Parng |
| 2007/0219728 A1 | 9/2007 | Papageorgiou et al. |

FOREIGN PATENT DOCUMENTS

| | | |
|---|---|---|
| WO | WO02059010 A1 | 8/2002 |
| WO | WO2004031749 A2 | 4/2004 |
| WO | WO2007050539 A2 | 5/2007 |

OTHER PUBLICATIONS

Potyrailo et al., "Optical Waveguide Sensors in Analytical Chemistry: Today's Instrumentation, Applications and Trends for Future Development", Fresenius' J. Anal. Chem., vol. 362, pp. 349-373, 1998.

Potyrailo et al., "Polymeric Sensor Materials: Toward an Alliance of Combinatorial and Rational Design Tools", Angew. Chem. Int. Ed., vol. 45, pp. 702-723, 2006.

Dickinson et al., "Generating Sensor Diversity Through Combinatorial Polymer Synthesis", Anal. Chem., vol. 69, No. 17, pp. 3413-3418, Sep. 1, 1997.

Apostolidis et al., "A Combinatorial Approach for Development of Materials for Optical Sensing of Gases", J. Comb. Chem., vol. 6, pp. 325-331, 2004.

Chojnacki et al., "Combinatorial Approach Towards Materials for Optical Ion Sensors", Microchimica Acta, vol. 147, pp. 87-92, 2004.

Potyrailo et al., "Analytical Instrumentation Infrastructure for Combinatorial and high-Throughput Development of Formulated Discrete and Gradient Polymeric Sensor Materials Arrays", Review of Scientific Instruments, vol. 76, pp. 062225-1-062225-9, 2005.

WTW, "New Instruments", www.WTW.com, 5 pages.

Sensicore: Product Information Systems, www.sensicore.com, 1 page.

Horiba Water Quality Analyzers, www.jp.horiba.com, 2 pages.

Hach Company, "Water Quality Testing Instruments and Reagents for Laboratory", www.hach.com, 1 page.

Mitchell Instrumetn Company, Inc., "Electrical Test and Measurement, Calibration", http://mitchellinstrument.com, 4 pages.

Analyticon Instruments Corporation, www.analyticon.com, 6 pages.

"Fused Quartz Properties & Usage Guide", http://www.quartz.com/gedata/html, 10 pages, Feb. 23, 1996.

Chile Search Report.

PCT International Search Report dated Jun. 8, 2009.

* cited by examiner

ARTICLE, DEVICE, AND METHOD

CROSS-REFERENCE TO RELATED APPLICATIONS

This application is a non-provisional application that claims priority to provisional U.S. Pat. application Ser. No. 60/955,823 filed on Aug. 14, 2007; the disclosure of which is hereby incorporated by reference.

BACKGROUND

1. Technical Field

The invention includes embodiments that relate to an article for use in a detector device, and to the detector device. The invention includes embodiments that relate to a method of using the article or detector device.

2. Discussion of Art

A microfluidic detector system can analyze small amounts of sample that is introduced into the system. The sample may include one or more analytes of interest. The microfluidic detector system may have components that include a propulsion device, flow controls, flow conditioning components, energy sources, and detectors of changes of analytes in response to the measured parameter or parameters. The propulsion device may be a pump; the flow controls may include valves and filters; the flow conditioning components may include heaters and coolers; and, the detectors may include optical, thermal, electrochemical-based detectors.

The microfluidic detector system may use fluidic pumps and/or syringes to provide an amount of the sample into a testing area where the sample can be tested. The complexity of the tubing and/or robotics that move and meter the sample, and that clean and purge the testing area between use, may be problematic. Further, the microfluidic detector system may be unwieldy in size and may not be amenable to portability and field use.

It may be desirable to have a device or system with properties and characteristics that differ from those properties of currently available apparatus or system. It may be desirable to have a method that differs from those methods currently available.

BRIEF DESCRIPTION

In one embodiment, an article includes a substrate assembly for use in a detector system. The substrate assembly includes a substrate; a sample reception structure secured to the substrate; a test window extending through the substrate; and a fluid channel defined by a surface of the substrate and extending from the sample reception structure to the test window.

In one embodiment, a device is provided in combination with the article. The device includes a housing having an interior surface defining a chamber capable of receiving the article, an energy source, and a detector. The energy source and the detector align with at least one test window of the article when the article is received in the housing chamber.

DETAILED DESCRIPTION

Figure 1:
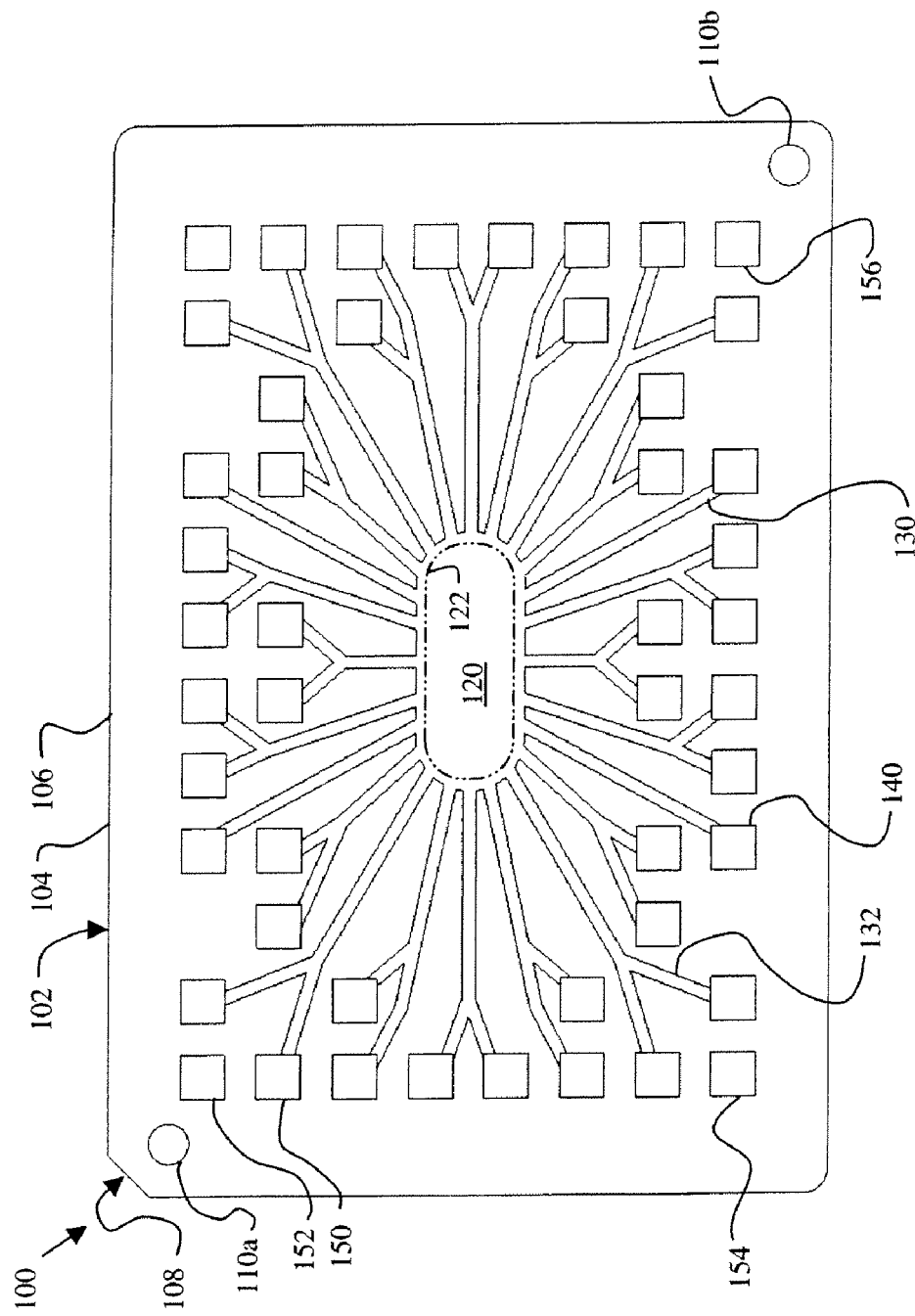
FIG. 1 schematically illustrates a substrate assembly according to an embodiment of the invention.

The invention includes embodiments that relate to an article for use in testing a sample containing an analyte. The article may be placed in a detector that tests the article.

As used herein, the terms "may" and "may be" indicate a possibility of an occurrence within a set of circumstances; a possession of a specified property, characteristic or function; and/or qualify another verb by expressing one or more of an ability, capability, or possibility associated with the qualified verb. Accordingly, usage of "may" and "may be" indicates that a modified term is apparently appropriate, capable, or suitable for an indicated capacity, function, or usage, while taking into account that in some circumstances the modified term may sometimes not be appropriate, capable, or suitable.

The term transparent is defined as greater than 90 percent transmission of the electromagnetic radiation indicated. If no electromagnetic radiation or energy is specified, visible light is intended. The term fluid, as used herein, includes liquid, vapor, or gas as appropriate for the circumstance; and, can refer to aqueous samples, oil-based samples, and biologically-derived fluids as appropriate for the circumstance.

In one embodiment, an article is provided that includes a substrate assembly for use in a detector system. The substrate assembly includes a substrate, a sample reception structure secured to the substrate, and a test window extending through the substrate. A fluid channel is defined by a surface of the substrate. The fluid channel extends from the sample reception structure to the test window.

Suitable substrates may be formed from inorganic materials or from organic materials depending on such factors as the type of fluid to be sampled, and the type of analyte to be measured. In one embodiment, the substrate includes an ultraviolet (UV) transparent material. One suitable substrate material may include a quartz material. In one embodiment, the substrate may be at least 99 percent opaque in regions of the substrate that are not in the area of the test window.

Suitable polymeric material for use as the substrate may include polyolefin, siloxane, polycarbonate, or polyetherimide. A suitable polyolefin may include polyethylene, polypropylene, or halogenated derivatives thereof. Other substrates may be dissolvable, degradable or dispersible; these substrates may be formed from hydroxypropyl cellulose or low molecular weight (MW) polyethylene glycols.

Shaping of the article may affect performance in some instances. At the very least, a shaped article may be configured with reference to a receiving portion of the detector. One suitable shape may be polygonal. The polygonal article may define three or more corners. By configuring at least one corner, a user may guide alignment of the substrate assembly in the detector system. Registration of the substrate assembly relative to the energy source and the detector may enhance measurement accuracy and reproducibility. The substrate may have a surface that defines one or more apertures capable of registering the location of the substrate assembly within the detector system.

The sample reception structure may be shaped to affect fluid flow into and through the channels. The sample reception structure has an inner surface that defines a plurality of fluid egress ports coupled to the flow path. In one embodiment, the sample reception structure may have a oblate cross-sectional profile, a circular cross-sectional profile or a polygonal cross-sectional profile. Selection of the sample reception structure configuration may affect such parameters as flow volume, fluid distribution, flow rate, and sample size. The inner surface may have an inverted frusto-conical shape defined by sidewalls, while other sidewall orientations may be available. The slope, texture, and composition of the sidewalls may affect the above-identified parameters.

With regard to the test window, suitable test windows may be transparent to electromagnetic radiation of a determined wavelength. In one embodiment, the test window has a transparency of greater than about 90 percent for light having a wavelength of about 463 nanometer, 525 nanometers, 630 nanometers, or 780 nanometers. In another embodiment, the test window has a transparency of greater than about 90 percent for light having a wavelength of greater than about 420 nanometers. In another embodiment, the test window has a transparency of greater than about 90 percent for light having a wavelength of less than about 900 nanometers. In yet another embodiment, the test window has a transparency of greater than about 90 percent for light having a wavelength of greater than about 220 nanometers.

The test window may include a functionalized surface. The functionalized surface may have a hydroxyl, silanol, amine, or aldehyde pendant group. A hydrogel may be secured to the functionalized surface. The hydrogel may include a material selected from poly(hydroxy ethyl methacrylate), poly(acrylic acid), poly(methacrylic acid), poly(glyceryl methacrylate), poly(vinyl alcohol), poly(ethylene oxide), poly(acrylamide), poly(N-acrylamide), poly(N,N-dimethyl amino propyl-N'-acrylamide), poly(ethylene imine), sodium poly(acrylate), potassium poly(acrylate), polysaccharide, and poly(vinyl pyrrolidone); or, copolymers of two or more thereof. The hydrogel layer may have a thickness greater than about 0.1 micrometer. The hydrogel layer may have a thickness of less than about 200 micrometers. In one embodiment, the hydrogel layer thickness may be in a range of from about 1 micrometer to about 50 micrometers, from about 50 micrometers to about 100 micrometers, or from about 100 micrometers to about 200 micrometers.

In one embodiment, the test window includes a film. The film may include one or more reactive materials. In one embodiment, the film includes, or is, the hydrogel layer. The film may further include an optically reactive material and one or more modifiers. The modifiers may be capable of modifying one or more of a selectivity of the film response to one or more analytes of interest, a dynamic range of response of the film, a detection limit of response of the film, a spectral color of response of the film, a stability of response of the film, a linearity of response of the film, or a response time of the film.

The reactive material may react with at least one of hydronium ions, hydroxide ions, halogen ions, metal ions, or monomers. The metal ions may include calcium or magnesium. Other metal ions may include aluminum, arsenic, cadmium, copper, lead, iron, manganese, or zinc. The reactive material may react with at least one of carbonate ions, bicarbonate ions, phosphate ions, phosphite ions, sulphate ions, or sulphite ions. The reactive material may react with at least one of polyacrylic acid, polysulfonated monomer, or maleic anhydride. The reactive material may react with an anionic polymer. The reactive material may react with a biological agent or a bioactive agent.

The reactive material may include analyte-specific reagents. As used herein, "analyte-specific reagents" are compounds that exhibit change in colorimetric, photorefractive, photochromic, thermochromic, fluorescent, elastic scattering, inelastic scattering, polarization, and any other optical property useful for detecting physical, chemical and biological species. Analyte-specific reagents may include metal complexes or salts, organic and inorganic dyes or pigments, nanocrystals, nanoparticles, quantum dots, organic fluorophores, inorganic fluorophores, and their combinations thereof.

Suitable reactive materials may include one or more organic dye, organic fluorophore, fluorescent dye, IR absorbing dye, UV absorbing dye, metachromatic dye, photochromic dye, thermochromic dye, or sulphonephthalein dye. Suitable reactive materials may include one or more of bromopyrogallol red, xylidyl blue I, chlorophosphonazo III, brilliant green, rhodamine B, rhodamine 6G, eosine, phloxine B, acridine orange, acridine red, ethyl red, methyl red, 3,3'-diethylthiacarbocyanine iodide, 3,3'-diethyloxadicarbocyanine iodide, merocyanine dye, methylene blue, bromothymol blue, bromocresol green, or phenol blue. Suitable reactive materials may include one or more of acridine dyes, anthracene dyes, azo dyes, catechol dyes, cyanine dyes, oxazine dyes, oxonol dyes, phthalo cyanine dyes, phenothiazine dyes, porphyrin dyes, styryl dyes, triaryl methane dyes, thiazine dyes, triphenyl methane dyes, or xanthene dyes. Suitable reactive materials may include one or more Cy3 green fluoresecent dye, Cy5 red fluoresecent dye, Cy5-labeled antisense ribonucleic acid. Suitable reactive materials may include one or more antibodies, enzymes, nucleic acids, aptazymes, or aptamers.

Suitable reactive materials may include one or more gold-nanoparticle labels capable of a color change from red to blue upon aggregation of the gold-nanoparticles. Suitable reactive materials may include a silver-staining agent capable of staining the gold-nanoparticle labels. Suitable reactive materials may include one or more of glycol, alkyl ethers, or vinyl alcohol.

The reactive material may include a metal complex and a dye. The metal complex may have a relatively high specificity to the analyte (phosphate in one case). Examples of suitable metal complexes may include zinc complexes and cobalt complexes. The metal complex may include at least one ligand capable of coordinating with the metal cation. The metal ligand complex is chosen such that it provides some geometrical preferences resulting in selective binding of anions of a particular shape. Examples of suitable ligands include pyridines, amines and any other nitrogen containing ligands. In one embodiment, a dinuclear zinc complex of (2,6-Bis(bis(2-pyridylmethyl)aminomethyl)-4-methyl-phenol) ligand was employed as the reactive material.

Metalochromic dyes are used along with the metal complexes. Some examples of metalochromic dyes that can be used with the metal complexes include catechol dyes, triphenylmethane dyes, thiazine dyes, oxazine dyes, anthracene dyes, azo dyes, phthalocyanine dyes, and combinations of two or more thereof. Some specific examples of metalochromic dyes include, but are not limited to, pyrocatechol violet, Murexide, Arsenazo I, Arsenazo III, Antipyrylazo III, Azo1, Acid Chrome Dark Blue K, BATA (bis-aminopehnoxy tetracetic acid), Chromotropic acid, and XB-I (3-(3-(2,4-dimethyl phenyl carbamoyl)-2-hydroxy naphthalen)-1-yl-azo)-4-hydroxy benzene sulfonic acid, and sodium salt.

A suitable metachromatic dye may include a cationic dye with a phenothiazine structure. Suitable phenothiazine dyes may include Dimethyl Methylene Blue, Basic Blue 17, and New Methylene Blue N. Structural examples of some suitable dyes are shown in Table 1.

TABLE 1

Metachromatic dyes.

Dimethyl Methylene Blue

Basic Blue 17

New Methylene Blue N

Additional materials included in with the reactive material on the test window include, for example, pH-Modifiers that serve as a buffer and maintain the pH level at a constant pH. The choice of pH-modifiers depends upon the nature of the analyte-specific reagent used, but pH-modifiers may include acids, bases, or salts.

Other additional materials may include a signal enhancer. Signal enhancers may mask free isopolymolybdates that may be difficult to distinguished from phosphomolybdate species. If not masked, the free isopolymolydbates may ion pair with the dyes resulting in a higher background signal or reduced signal due to phosphate alone. Examples of a suitable signal enhancer include, but are not limited to, oxalic acids, sulfonic acids, oxalates, sulfonates, and a combination of two or more thereof.

A surfactant may be added to the reactive material. Suitable surfactants include quaternary ammonium salts. Such salts may include cetyltrimethyl ammonium bromide, tridodecylmethyl ammonium chloride, and tetrabutyl ammonium bromide.

In one embodiment, a polymer may be added for enhancement of signal. The polymer concentration may be present in an amount in a determined range. A dye, 2-(2-(3-((1,3-Dihydro-3,3-dimethyl-1-propyl-2H-indol-2-ylidene)ethylidene)-2-phenoxy-1-cyclohexen-1-yl)ethenyl)-3,3-dimethyl-1-propylindolium perchlorate may be co-added. The dye is commercially available as IR 768 perchlorate. A suitable polymer addition may include commercially available NAFION brand membranes, or another proton exchange membrane.

With regard to the fluid channel, the channel has a height, a width, and a length. The height and the width may be selected to control a flow rate of a fluid therethrough, and the fluid has a viscosity and surface tension in a determined range within a set of determined operating conditions. The fluid channel may be further defined as an inner surface of a coating that lines a groove in the substrate. The coating may be formed from a material that is selected such that the fluid channel inner surface can control a flow rate of a fluid therethrough, where the fluid has a viscosity and surface tension in a determined range within a set of determined operating conditions.

The fluid channel may be one of a plurality of flow channels, and each flow channel of the plurality has a length that is selected to determine a flow time of a fluid from the sample reception structure to the test window, and the fluid has a viscosity and surface tension in a determined range within a set of determined operating conditions.

In one embodiment, the fluid channel defines a flow path that has no right angle turns and no acute angle turns. Additionally, the fluid channel may define a flow path that makes arcuate turns. The fluid channel may define at least one root flow path and at least two sub flow paths, and the sub flow paths each have a flow volume that is a fraction of the flow volume of the root flow path, and each sub flow path flow volume is selected to provide a determined amount of sample to the test window. The sub flow path may differ in flow volume from at least one other sub flow path for a single root flow path. In one embodiment, the fluid moves in the channel due to capillary action only. Alternatively, the fluid moves or is motivated by centrifugal action. Additionally, dynamic pressure may be applied by the column height of the sample fluid in the sample reception structure.

The substrate assembly may include an authentication segment. A suitable authentication segment may be a colorimetric region having a determined color, a holographic label, a bar code (2D or 3D), or an embedded chip. In one embodiment, the authentication segment is a radio frequency identification device (RFID). The RFID may be active or passive, and may communicate with an RFID reader in the detector unit.

The substrate assembly may have a "previous use" indicator secured thereto. The previous use indicator may function to identify a substrate assembly as having been used previous use. Suitable previous use indicators may include an optical region that irreversibly changes its optical property upon exposure to tested sample. Also included as a previous use indicator is a tamper indicator function. Such a previous use indicator may include a gas impermeable sealing film over an air-reactive structure in which removal of the film, required to access one or more test windows, also exposes the structure to atmospheric gas to cause a detectable change in the structure—e.g., an optical change. The status of the previous use indicator as either "used" or "not yet used" may be detectable by a sensor in the detector device.

The article may have a fluid overflow structure. The fluid overflow structure may be fluidically connected with test windows, but is at least coupled to the sample reception structure. The fluid overflow structure may ensure that a determined sample amount of test fluid, and no more, is provided to the test windows via the sample reception structure.

In one aspect, an embodiment of the invention provides a device that can receive the article, including the substrate assembly. The device in combination with the article comprises another embodiment of the invention. The device may include a housing having an interior surface. The interior surface may define at least a portion of a chamber that is sized and shaped to receive the article. The device may include an energy source and a detector. The energy source and the detector align with at least one test window of the article when the article is in the housing chamber.

The device can include a plurality of level adjustment mechanisms. The mechanisms may be manipulated to adjust the level of the substrate assembly in the housing chamber. Having the substrate assembly balanced may facilitate even, uniform, and/or proper distribution of sample fluid from the sample reception structure, through the sample channels to the test windows.

The device can include circuitry for powering the device from a battery, from a power adaptor, or from both. And, the circuitry may be able to dynamically shift from battery mode to power adaptor mode without disruption of a test procedure if such is in progress during a powering mode change.

The device can include a display screen. The screen may display information read by the detector related to a tested sample on the test window, or information related to a status of the device, or both.

Embodiments of the device may include a hinged lid. A surface of the lid may define a portion of the housing chamber. The lid can contain some optical components of the device. If a timing device is provided, a suitable location may include the lid. The timer may be useful for kinetic quantifications. Suitable optical components can include a sensor and/or a matching electromagnetic energy source. Suitable electromagnetic energy sources may include heat bars, lamps (e.g., tungsten lamp), ultraviolet light sources, light emitting diodes (red, green and/or blue), organic light emitting diodes, and laser diodes. Other suitable electromagnetic energy sources are listed in Table 2.

TABLE 2

Energy sources

| Source | Spectral range of emission (nm) |
|---|---|
| Continuous wave sources: | |
| Xenon arc lamp | 200-1000 |
| Mercury arc lamp | 250-600 |
| Deuterium lamp | 180-420 |
| Tungsten lamp | 320-2500 |
| Light emitting diodes | different diodes cover range from about 250 to 1500 nm |
| Diode lasers | different diode lasers cover range from about 400 to 1500 nm |
| Argon ion laser | several lines over 350-514 nm |
| Helium-neon laser | several lines over 543-633 nm |
| Krypton laser | several lines over 530-676 nm |
| Pulsed sources: | |
| Nitrogen laser | 337 nm |
| Nd:YAG laser | fundamental-1064, frequency doubled-532, tripled-355 |
| Ti:Sapphire laser | 720-1000, frequency doubled 360500 |
| Dye lasers | 360-990 frequency doubled 235 to 345 |

Suitable sensors or detectors may include photodetectors, photomultipliers, charge coupled devices, and the like. Examples of detectors include vacuum or solid state and single or multichannel detectors. Vacuum detectors are phototubes and photomultiplier tubes (PMT). Solid-state detectors include photodiodes, photodiode arrays, charge-coupled devices (CCDs), charge-injection devices (CIDs), and avalanche photodiodes. Multichannel detectors include arrays of individual detectors such as photodiode arrays, PMT arrays. Also, CCDs, CIDs, CMOS, and other types of multichannel detectors are available, and useful as appropriate.

The electromagnetic energy source (referred to herein sometimes as a light source) may be selected, and coupled with an appropriate sensor, so that a sample fluid in contact with a reactive material may affect the amount or type of energy emitted by the light source, interactive with the reactive material, and received by the sensor. The reactive material may react with an analyte in the sample fluid (liquid, vapor, or gas). That reaction may increase the light passing through the reactive material, may decrease the amount of light passing through the reactive material, or may change the wavelength of the light passing through the sample. Also, that reaction may increase the light reflecting off of the reactive material, may decrease the amount of light reflecting off of the reactive material, or may change the wavelength of the light reflecting off of the sample. Still also, the contact of energy from the source may cause signal molecules in the reactive material to fluoresce in the presence of the analyte.

And, depending on the selection of source, detector and reactive material, other interactions may occur—such as, Raman scattering in the presence of the analyte. For such an embodiment, the Raman active material may be picked up by the analyte during the sample fluid flow through the channel to the reactive material. In such a way, the Raman active particles (or another measurable/detectable signaling agent) are physically spaced from the test window unless moved there as carried by the analyte.

With regard to the notched or configured substrate discussed above, the device may include a protuberance that corresponds to a notch defined by some portion of the substrate assembly. Contact of the protuberance with the notch aligns the substrate assembly within the housing chamber in a determined location and orientation.

The device can include a base and a lid. The lid can be hingedly connected to the base. A surface of the lid and a surface of the base may cooperate with each other when the lid is closed to define the housing chamber.

The lid can contain optical components. Optical components can include energy sources and detectors. In one embodiment, the lid contains one or more detectors and the base contains the energy source. The energy source can supply electromagnetic energy to the detector. Alternatively, the base contains one or more detectors and the lid contains the energy source. Respective surfaces of the lid and the base can define at least one test cell with a determined light path that extends through a test window.

The device can include also a test cell length calibration device. The calibration device can be adjacent to at least one test cell, and can determine a length of the test cell. A distance-measuring laser emitter/detector can be used. With further regard to calibration, the substrate assembly can include a blank or a calibration test window through which at least one test cell extends. An additional test cell can be used as a reference, and that test cell does not extend through a test window. During operation, the device can sense and/or monitor the test cell length, the register of the substrate assembly, and other parameters that can affect measurement precision or accuracy. The monitoring can be done dynamically.

A sample amount sufficiency check device can be included in the device or in the substrate assembly, and can be associated with the sample reception structure or with the test window. As the name indicates, improper amounts of sample fluid can be detected by the check device. While an overflow structure can ensure that too much sample is not used, the check device may be useful for insufficiently small amounts of sample fluid.

Some reaction materials may need time to complete a reaction. Other reaction materials may benefit from applied energy to drive a reaction change. If reaction materials are used that require heat to form a sufficiently complete reaction, a thermal source may be supplied that is in thermal communication with the test window. The thermal source may supply thermal energy to the test window during a reaction period of operation. An electrically resistive coil, a heater bar, or an infrared source may be used.

For embodiments in which living organisms may contact the device, particularly the housing chamber surface, an antimicrobial coating may be disposed on the inner surface of the housing chamber. The antimicrobial coating may be continuous and transparent to the energy of interest as it passes over the energy source and detector. Where the sample fluid contains noxious materials (e.g., chemical weapons, toxins, pesticides, and the like) a coating that is resistive to, or capable of breaking down, the noxious material may be used.

With further reference to the optical components, the light source can create electromagnetic energy detectable by the detector, or that can excite a fluorescent material disposed on a test window. The light source can be a light emitting diode, an organic light emitting diode, or a laser diode. The light emitting diode, the organic light emitting diode, or the laser diode can be part of a set. The set can emit light in the red, green and blue wavelength range. Another light source can be an ultraviolet light emitter. Yet another light source can be an infrared light emitter. The device can include a combination of such, each performing a different test.

A suitable detector can be an ultraviolet, visible, or infrared detector as needed. In one embodiment, the detector is a charge coupled device (CCD). In one embodiment, the detector is a photomuliplier tube. The detector can be aligned and oriented such that energy emitted from the energy source travels through the test window, interacts with the sensing film and travels to the detector. Alternatively, the detector can be aligned and oriented such that energy emitted from the energy source travels through the test window, interacts with the sensing film and travels back to the detector. The energy source and the detector can be on the same side of the test window as a sensing film being tested, or the energy source and the detector are on an opposing side of the test window as a sensing film being tested.

In one embodiment, there may be one light source with a plurality of detectors. The plurality of detectors may include spectral detectors.

With reference to FIG. 1, an article 100 according to an embodiment of the invention is shown. The article includes a substrate assembly 102. The substrate assembly 102 includes a substrate 104 having a peripheral edge 106. The peripheral edge defines a notched corner 108. A surface of the substrate defines first and second register apertures 110a, 110b that align and orient the substrate assembly within the detector (see FIG. 3). A sample reception structure 120 is about centered on the substrate. In the illustrated embodiment, the sample reception structure is oblate or oval. A plurality of egress ports 122 allow the sample structure to communicate with a corresponding plurality of root fluid channels 130. At least some of the root fluid channels divide into sub channels 132. The fluid channels allow fluid communication of the sample reception structure to test windows 140.

A sample amount sufficiency test cell 150, a reference test cell 152, a previous use indicator 154, and an authentication segment 156 are provided on the substrate.

Figure 2:
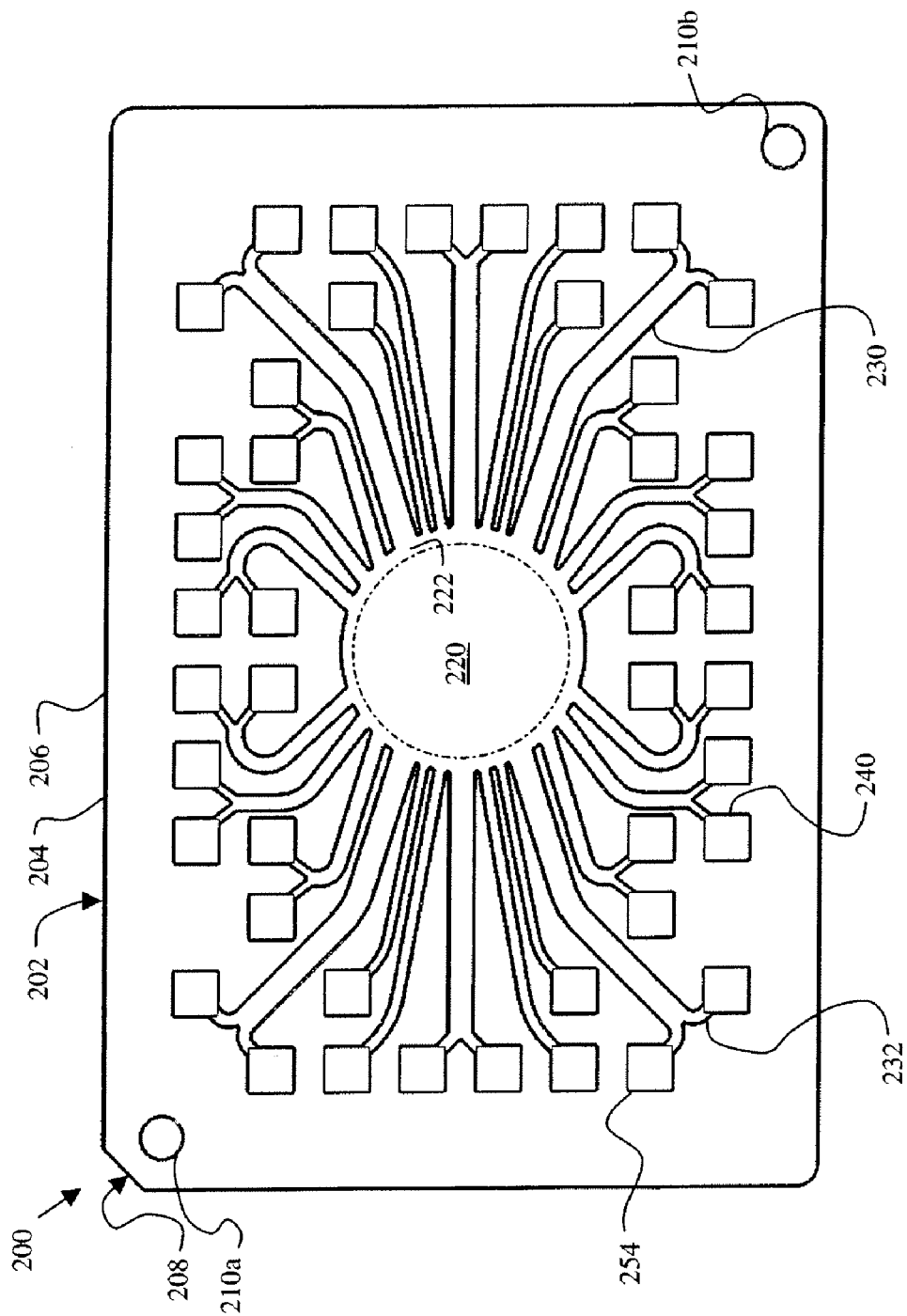
FIG. 2 schematically illustrates another substrate assembly according to an embodiment of the invention.

With reference to FIG. 2, an article 200 according to an embodiment of the invention is shown. The article includes a substrate assembly 202. The substrate assembly includes a substrate 204 having a peripheral edge 206. The peripheral edge defines a notched corner 208. A surface of the substrate defines first and second register apertures 210a, 210b that align and orient the substrate assembly within the detector. A sample reception structure 220 is about centered on the substrate. In the illustrated embodiment, the sample reception structure is oblate or oval. A plurality of egress ports 222 allow the sample structure to communicate with a corresponding plurality of root fluid channels 230. At least some of the root fluid channels divide into sub channels 232. The fluid channels allow fluid communication of the sample reception structure to test windows 240. A tamper indicator 254 is provided on the substrate.

In this illustrated embodiment, the sample reception structure has a circular cross-sectional profile or is round. The fluid channels are arcuate and do not define sharp angles or turns. Further, the fluid channels have differing widths so that fluid flow rate and/or fluid flow volume through the differing channels is controlled and determined to be independent of each other. In alternative embodiments, the fluid channels may be angled to induce a determined amount of mixing to the fluid flow.

After use, the substrate may be retrieved and disposed of. The inside of the housing may be disinfected, decontaminated and sterilized as appropriate.

EXAMPLES

Example 1

Quantitative Analysis of Chemical Species (Analytes) in Water

The device can provide water analysis. The device is blanked without a substrate assembly within the housing chamber. After blanking, a substrate assembly is placed in the housing chamber and a zero reading or calibration is performed. Then, a water sample (<50 µL volume) is applied onto the substrate assembly into the sample reception structure. The substrate assembly has a plurality of test windows that include a film with a differing reactive material on each window. The fluid moves from the sample reception structure through fluid flow channels and contacts the reactive material films on the test windows. After 2 minutes of exposure light is emitted from an energy source, passes through the test window, film, reactive material, and fluid sample and is detected by a detector. A static measurement is made at one test window, a series of measurements are made over determined time periods through another test window for dynamic data capture. The detected light amounts are saved in a computer memory for analysis and evaluation.

In one test window, a determination of $Ca^{2+}$ is made. The reactive material in the sensing film incorporates a $Ca^{2+}$ ion-sensitive dye, Xylidyl Blue, in a poly-(2-hydroxyethy) methacrylate hydrogel. The calibration curve for the $Ca^{2+}$ determination has a shape typical to determinations of cations using organic chromogenic dyes immobilized in polymeric films. The calculated detection limit (at S/N=3) is 5 parts per million (ppm). This detection limit corresponds to a 0.023 absorbance units resolution as obtained by measurement of the same colorimetric films with a comparative portable optical spectrometer.

In another test window, a determination of chlorine in water is performed. The sample fluid contacts another reactive material in another sensing films that contains 1',1'-diethyl-4,4'-carbocyanine iodide dye in poly(2-hydroxyethy) methacrylate) hydrogel. A calculated detection limit for chlorine determinations (at S/N=3) is 200 parts per billion (ppb).

Example 2

Biological Sampling

A test window is prepared with a film having a reactive material incorporated therein. The reactive material includes a biorecognition molecule that is an immobilized antibody that can complex an analyte of interest. Another test window has a film containing an immobilized oligonucleotide base pair hybridized with specific nucleic acid strands. The film includes additional enzymes suitable for use in an ELISA assay (alkaline phosphates and horseradish peroxidase), and a fluorescence-based detection mechanism. Similarly, the immobilized reagents contain an analyte or cofactor that stimulates a specific enzymatic reaction.

The detector includes a commercially available bifurcated fiber-optic reflection probe and the light source was a laser diode.

Addition of sample fluid to the sample reception structure causes determined amounts of sample fluid containing the analyte to flow to through the channels to the test windows. The channels, lined with immobilized species of antibodies, may selectively react with, and thus immobilize, interfering species from the sample fluid. The analyte, arriving at the test window, may react with a fluorophore so that when irradiated with a particular wavelength of light, emits light at a separate wavelength of light. The sensor/detector then monitors for the light at the second wavelength. The amount of light being based on the amount of analyte present in the sample at a particular concentration.

The embodiments described herein are examples of articles, systems, and methods having elements corresponding to the elements of the invention recited in the claims. This written description may enable those of ordinary skill in the art to make and use embodiments having alternative elements that likewise correspond to the elements of the invention recited in the claims. The scope of the invention thus includes articles, systems and methods that do not differ from the literal language of the claims, and further includes other articles, systems and methods with insubstantial differences from the literal language of the claims. While only certain features and embodiments have been illustrated and described herein, many modifications and changes may occur to one of ordinary skill in the relevant art. The appended claims cover all such modifications and changes.

The invention claimed is:

1. An article comprising a substrate assembly for use in a detector system, comprising:
   a substrate configured for use in the detector system;
   a sample reception structure secured to the substrate or formed integrally from a portion of the substrate;
   an optically transmissive test window extending through the substrate;
   a film secured to a surface of the optically transmissive test window and including one or more reactive materials formulated to provide a specific film performance; and
   a fluid channel defined by a surface of the substrate and extending from the sample reception structure to the test window, wherein the fluid channel is configured to control a flow rate of a fluid therethrough within a set of determined operating conditions.

2. The article as defined in claim 1, wherein the substrate comprises a material that is greater than 90 percent transparent to ultraviolet radiation.

3. The article as defined in claim 1, wherein the substrate comprises quartz material.

4. The article as defined in claim 1, wherein the substrate comprises a polymeric material selected from the group consisting of polyolefin, siloxane, polycarbonate, and polyetherimide.

5. The article as defined in claim 1, wherein the substrate is a polyolefin selected from the group consisting of polyethylene, polypropylene, and halogenated derivatives thereof.

6. The article as defined in claim 1, wherein the substrate has a polygonal cross-sectional profile defining three or more corners, and at least one corner is configured to guide alignment of the substrate assembly in the detector system.

7. The article as defined in claim 1, wherein the substrate has a surface that defines one or more apertures capable of registering the location of the substrate assembly within the detector system.

8. The article as defined in claim 1, wherein the sample reception structure has a oblate cross-sectional profile.

9. The article as defined in claim 1, wherein the sample reception structure has a circular cross-sectional profile or a polygonal cross-sectional profile.

10. The article as defined in claim 1, wherein the sample reception structure has an inner surface that defines a plurality of fluid egress ports coupled to the flow path.

11. The article as defined in claim 10, wherein the inner surface defines an inverted frusto-conical shape.

12. The article as defined in claim 1, wherein the test window is transparent to electromagnetic radiation of a determined wavelength.

13. The article as defined in claim 12, wherein the test window has a transparency of greater than about 90 percent for light having a wavelength of about 463 nanometer, 525 nanometers, 630 nanometers, or 780 nanometers.

14. The article as defined in claim 1, wherein the test window comprises a functionalized surface having a hydroxyl, silanol, amine, or aldehyde pendant group.

15. The article as defined in claim 1, wherein the film is a hydrogel secured to the functionalized surface.

16. The article as defined in claim 1, wherein the one or more reactive materials are capable of reacting with a biological agent or a bioactive agent.

17. The article as defined in claim 1, wherein one or more reactive materials comprises one or more organic dye, organic fluorophore, fluorescent dye, IR absorbing dye, UV absorbing dye, metachromatic dye, photochromic dye, thermochromic dye, or sulphonephthalein dye.

18. The article as defined in claim 1, wherein the fluid channel has a height, a width, and a length, and the height and the width are selected to control a flow rate of a fluid therethrough, and the fluid has a viscosity and surface tension in a determined range within a set of determined operating conditions.

19. The article as defined in claim 1, wherein the fluid channel comprises a material that is selected such that the fluid channel inner surface can control a flow rate of a fluid therethrough, and the fluid has a viscosity and surface tension in a determined range within a set of determined operating conditions.

20. The article as defined in claim 1, wherein the fluid channel is one of a plurality of flow channels, and each flow channel of the plurality has a length that is selected to determine a flow time of a fluid from the sample reception structure to the test window, and the fluid has a viscosity and surface tension in a determined range within a set of determined operating conditions.

21. The article as defined in claim 1, wherein the fluid channel defines a flow path that makes arcuate turns.

22. The article as defined in claim 1, wherein the fluid channel defines at least one root flow path and at least two sub flow paths, and the sub flow paths each have a flow volume that is a fraction of the flow volume of the root flow path, and each sub flow path flow volume is selected to provide a determined amount of sample to the test window.

23. The article as defined in claim 1, wherein at least one sub flow path differs in flow volume from at least one other sub flow path for a single root flow path.

* * * * *